(12) United States Patent
Neumann

(10) Patent No.: US 11,157,822 B2
(45) Date of Patent: Oct. 26, 2021

(54) METHODS AND SYSTEMS FOR CLASSIFICATION USING EXPERT DATA

(71) Applicant: Kenneth Neumann, Lakewood, CO (US)

(72) Inventor: Kenneth Neumann, Lakewood, CO (US)

(73) Assignee: KPN INNOVATONS LLC, Lakewood, CO (US)

( * ) Notice: Subject to any disclaimer, the term of this patent is extended or adjusted under 35 U.S.C. 154(b) by 0 days.

(21) Appl. No.: 16/397,814

(22) Filed: Apr. 29, 2019

(65) Prior Publication Data

US 2020/0342332 A1    Oct. 29, 2020

(51) Int. Cl.
*G06N 5/04* (2006.01)
*G06F 16/338* (2019.01)
*G06F 16/35* (2019.01)
*G06N 20/00* (2019.01)
*G06K 9/62* (2006.01)

(52) U.S. Cl.
CPC ............ *G06N 5/04* (2013.01); *G06F 16/338* (2019.01); *G06F 16/358* (2019.01); *G06K 9/6256* (2013.01); *G06N 20/00* (2019.01)

(58) Field of Classification Search
CPC ....... G16H 50/20; G06F 19/30; G06F 19/324; G06F 19/325; G06F 19/3418; G06F 19/3456; G06F 19/3475; G06F 19/36; G06F 16/338; G06F 16/358; G06N 20/00; G06N 5/04; G06K 9/6256
See application file for complete search history.

(56) References Cited

U.S. PATENT DOCUMENTS

| | | | |
|---|---|---|---|
| 6,802,810 B2 | 10/2004 | Ciarniello et al. | |
| 8,594,948 B2 | 11/2013 | McGlennen et al. | |
| 8,655,817 B2 | 2/2014 | Hasey et al. | |
| 8,812,244 B2 | 8/2014 | Angelides | |
| 9,092,391 B2 | 7/2015 | Stephan et al. | |

(Continued)

OTHER PUBLICATIONS

Chui, et al., Disease Diagnosis in Smart Healthcare: Innovation, Technologies and Applications, journal, Dec. 18, 2017, vol. 9, issue 12.

(Continued)

*Primary Examiner* — Kamran Afshar
*Assistant Examiner* — Marshall L Werner
(74) *Attorney, Agent, or Firm* — Caldwell Intellectual Property Law, LLC

(57) ABSTRACT

A system for classification using expert data includes at least a server. The system includes an expert submission processing module operating on the at least a server, the expert submission processing module designed and configured to receive at least an expert submission relating constitutional data to ameliorative recommendation data. The system includes a model generator operating on the at least a server, the model generator designed and configured to generate, using the at least an expert submission, and a constitutional inquiry, an ameliorative output. The system includes a client-interface module operating on the at least a server, the client-interface module designed and configured to receive, from a user client device, the constitutional inquiry and transmit, to the user client device, the ameliorative output.

20 Claims, 7 Drawing Sheets

(56) References Cited

U.S. PATENT DOCUMENTS

| | | | |
|---|---|---|---|
| 10,152,702 B2 | 12/2018 | Ingber | |
| 2004/0122790 A1 | 6/2004 | Walker et al. | |
| 2005/0075543 A1 | 4/2005 | Calabrese | |
| 2008/0059224 A1 | 3/2008 | Schechter | |
| 2014/0162887 A1 | 6/2014 | Martin et al. | |
| 2014/0279746 A1 | 9/2014 | De Bruin et al. | |
| 2015/0019241 A1 | 1/2015 | Bennett et al. | |
| 2015/0177250 A1 | 6/2015 | Leontovich et al. | |
| 2016/0140320 A1* | 5/2016 | Moturu | G16H 50/30 434/236 |
| 2017/0235912 A1* | 8/2017 | Moturu | G16H 50/50 705/2 |
| 2017/0236281 A1 | 8/2017 | Dacosta | |
| 2017/0329933 A1* | 11/2017 | Brust | G06F 16/24575 |
| 2018/0137249 A1 | 5/2018 | Eggebraaten et al. | |
| 2018/0315488 A1* | 11/2018 | Miranda | G16H 50/30 |
| 2018/0365383 A1 | 12/2018 | Bates | |
| 2019/0019582 A1* | 1/2019 | Wallis | G06N 3/08 |
| 2019/0057322 A1* | 2/2019 | Desiraju | A23K 10/18 |
| 2019/0088366 A1 | 3/2019 | Vaughan et al. | |
| 2019/0110754 A1 | 4/2019 | Rao et al. | |
| 2019/0206518 A1* | 7/2019 | Banerjee | G16H 80/00 |

OTHER PUBLICATIONS

PCT/US20/20973, International Search Report, dated Jun. 10, 2020.

\* cited by examiner

METHODS AND SYSTEMS FOR CLASSIFICATION USING EXPERT DATA

FIELD OF THE INVENTION

The present invention generally relates to the field of machine learning. In particular, the present invention is directed to methods and systems for classification using expert data.

BACKGROUND

Analytical processes assessing expert data have thus far been overwhelmed by an increasing quantity and diversity of source material. This furnishes a volume and heterogeneity of data that frustrates attempts at unified presentation; the result can be a dangerous lack of guidance, particularly where the data concerns a critical subject such as constitutional status and amelioration thereof.

SUMMARY OF THE DISCLOSURE

In one aspect, a system for classification using expert data includes at least a server. The system includes an expert submission processing module operating on the at least a server, the expert submission processing module designed and configured to receive at least an expert submission relating constitutional data to ameliorative recommendation data. The system includes a model generator operating on the at least a server, the model generator designed and configured to convert the at least an expert submission into training data. The system includes an expert learner operating on the at least a server, wherein the expert learner is configured to generate, using a machine learning process, an ameliorative output as a function of the training data and a constitutional inquiry. The system includes a client-interface module operating on the at least a server, the client-interface module designed and configured to receive, from a user client device, the constitutional inquiry and transmit, to the user client device, the ameliorative output.

In another aspect, a method of classification using expert data includes receiving, by at least a server, at least an expert submission relating constitutional data to ameliorative recommendation data and a constitutional inquiry, converting, by the at least a server, the at least an expert submission into training data, generating, by the at least a server, using machine learning, an ameliorative output as a function of the constitutional inquiry and the training data, and transmitting, by the at least a server and to a user client device, the ameliorative output.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments of systems and methods disclosed herein collect data from one or more experts and use the collected data to generate ameliorative outputs in response to constitutional inquiries; this may be used to indicate optimal ameliorative outputs for given constitutional data. Generation may be performed using machine-learning processes, including without limitation conversion of at least an expert submission into training data, which may be used to generate models and/or drive lazy loading processes.

Figure 1:
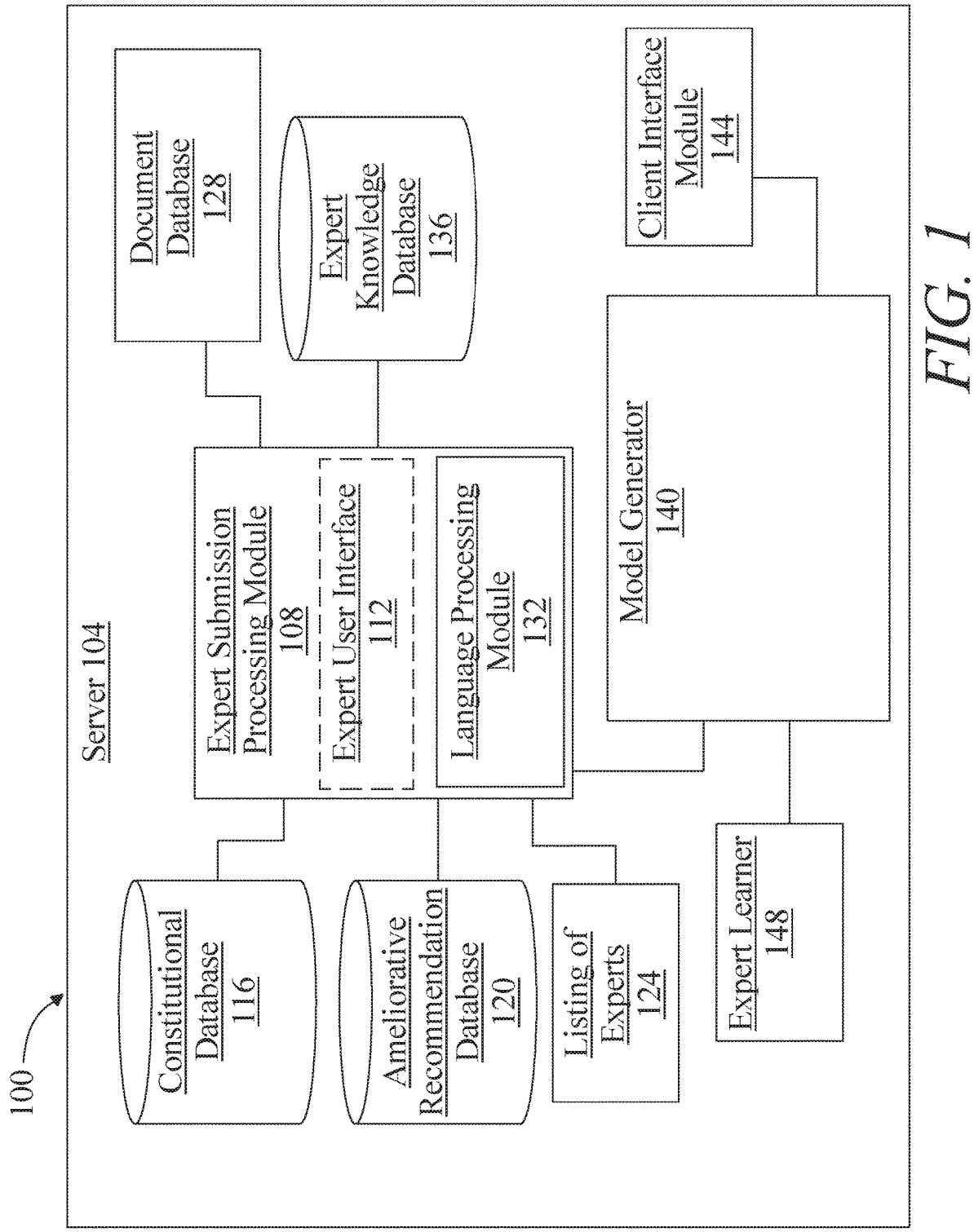
FIG. 1 is a block diagram illustrating an exemplary embodiment of a system for classification using expert submissions.

Referring now to the FIG. 1, an exemplary embodiment of a system 100 for classification using expert data is illustrated. System 100 includes a at least a server 104. At least a server 104 may include any computing device as described in this disclosure, including without limitation a microcontroller, microprocessor, digital signal processor (DSP) and/or system on a chip (SoC) as described in this disclosure. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

Still referring to FIG. 1, at least a server 104 and/or one or more modules operating thereon may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, system 100 includes an expert submission processing module 108 operating on the at least a server 104. Expert submission processing module 108 may include any hardware or software module as described in this disclosure; any module as described herein may be created using any combination of hardware and/or software logic commands, and may be physically or conceptually separate from or merged with any other such module, as persons skilled in the art will appreciate upon reviewing the entirety of this disclosure. Expert submission processing module 108 is designed and configured to receive at least an expert submission relating constitutional data to ameliorative recommendation data. At least an expert submission may include a single expert submission and/or a plurality of submissions; plurality of submissions may be received from a plurality of experts as described below. Plurality of experts may represent a set of most highly regarded and/or influential experts for a given field or area of expertise and may be selected according to methods described in further detail below. As used in this disclosure, constitutional data includes any data relating to a constitution of a person. Constitutional data may include physiological state data.

Still referring to FIG. 1, physiological state data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibronigen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain. Physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

Continuing to refer to FIG. 1, constitutional data may include one or more prognostic labels. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

Continuing to refer to FIG. 1, constitutional data may include current ameliorative data. As used in this disclosure, current ameliorative data is data identifying at least a process that tends to improve a physical condition of a user, where a physical condition of a user may include, without limitation, any physical condition identifiable using a prognostic label. Current ameliorative data may include, without limitation, exercise programs, including amount, intensity, and/or types of exercise recommended. Current ameliorative data may include, without limitation, dietary or nutritional recommendations based on data including nutritional content, digestibility, or the like. Current ameliorative data may include one or more medical procedures. Current ameliorative data may include one or more physical, psychological, or other therapies. Current ameliorative data may include one or more medications. Persons skilled in the art, upon reviewing the entirety of this disclosure, will be aware of various processes that may be used as current ameliorative data consistently with this disclosure.

Still referring to FIG. 1, expert submission processing module 108 is configured to receive ameliorative recommendation data. Ameliorative recommendation data may include any prognostic and/or ameliorative data, as described above, suggested by "best practices" according to expert submissions. For instance, and without limitation, an expert may provide an entry in which ameliorative recommendation data indicates that a given symptom, biomarker, or other element of physiological state data is caused by or correlated with one or more prognostic labels corresponding to probable current and/or future medical conditions. As a further example, an expert may provide ameliorative recommendation data indicating that a given element or set of physiological state data and/or prognostic label data should be treated according to one or more ameliorative processes and/or therapies. In the aggregate, at least an expert submission may include a plurality of such ameliorative recommendation data, which may differ from one another; for instance, one expert submission may recommend a first set of ameliorative processes, and a second expert submission may recommend a second set of ameliorative processes, which may include some ameliorative processes recommended in the first set, exclude some ameliorative processes recommended in the first set, and/or include one or more ameliorative processes not present in the first set. Aggregations of expert submissions may be subjected to tallying, ranking, and/or machine learning processes as described in further detail below.

In an embodiment, and continuing to refer to FIG. 1, expert submission processing module 108 may include an expert user interface 112 designed and configured to configure an expert client device to display one or more data entry fields prompting an expert to input expert submission data and receive, from the expert client device, at least a datum entered in the one or more data entry fields by the expert. Expert user interface 112 may include without limitation a form or other graphical element having data entry fields, wherein one or more experts, including without limitation clinical and/or scientific experts, may enter information describing constitutional data and/or ameliorative recommendation data; fields in expert user interface 112 may provide options describing previously identified constitutional data and/or ameliorative recommendation data, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest constitutional data and/or ameliorative recommendation data not currently recorded. Expert user interface 112 or the like may include fields corresponding to prognostic and/or ameliorative data, where experts may enter data describing prognostic and/or ameliorative data and/or categories of prognostic and/or ameliorative data the experts consider related to and/or recommended for constitutional data. Fields for entry of constitutional data and/or ameliorative recommendation data may include free-form data entry fields such as text entry fields; as described above, examiners may enter data not presented in pre-populated data fields in the free-form data entry fields. Alternatively or additionally, data entry fields may enable an expert to select and/or enter information describing or linked to constitutional data and/or ameliorative recommendation data that the expert considers significant and/or preferable, where significance may indicate likely impact on longevity, mortality, quality of life, or the like as described in further detail below. Expert user interface 112 may provide an expert with a field in which to indicate a reference to a document describing constitutional data and/or ameliorative recommendation data as described in further detail below.

Still referring to FIG. 1, data used to auto-populate fields and/or to be matched to textual entries may be stored in one or more databases. As a non-limiting example, one or elements of constitutional data may be stored in and/or retrieved from a constitutional database 116. A constitutional database 116 may include any data structure for ordered storage and retrieval of data, which may be implemented as a hardware or software module. A constitutional database 116 may be implemented, without limitation, as a relational database, a key-value retrieval datastore such as a NOSQL database, or any other format or structure for use as a datastore that a person skilled in the art would recognize as suitable upon review of the entirety of this disclosure. A constitutional database 116 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a constitutional database 116 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of constitutional data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a constitutional database 116 may reflect categories, cohorts, and/or populations of data consistently with this disclosure.

Figure 2:
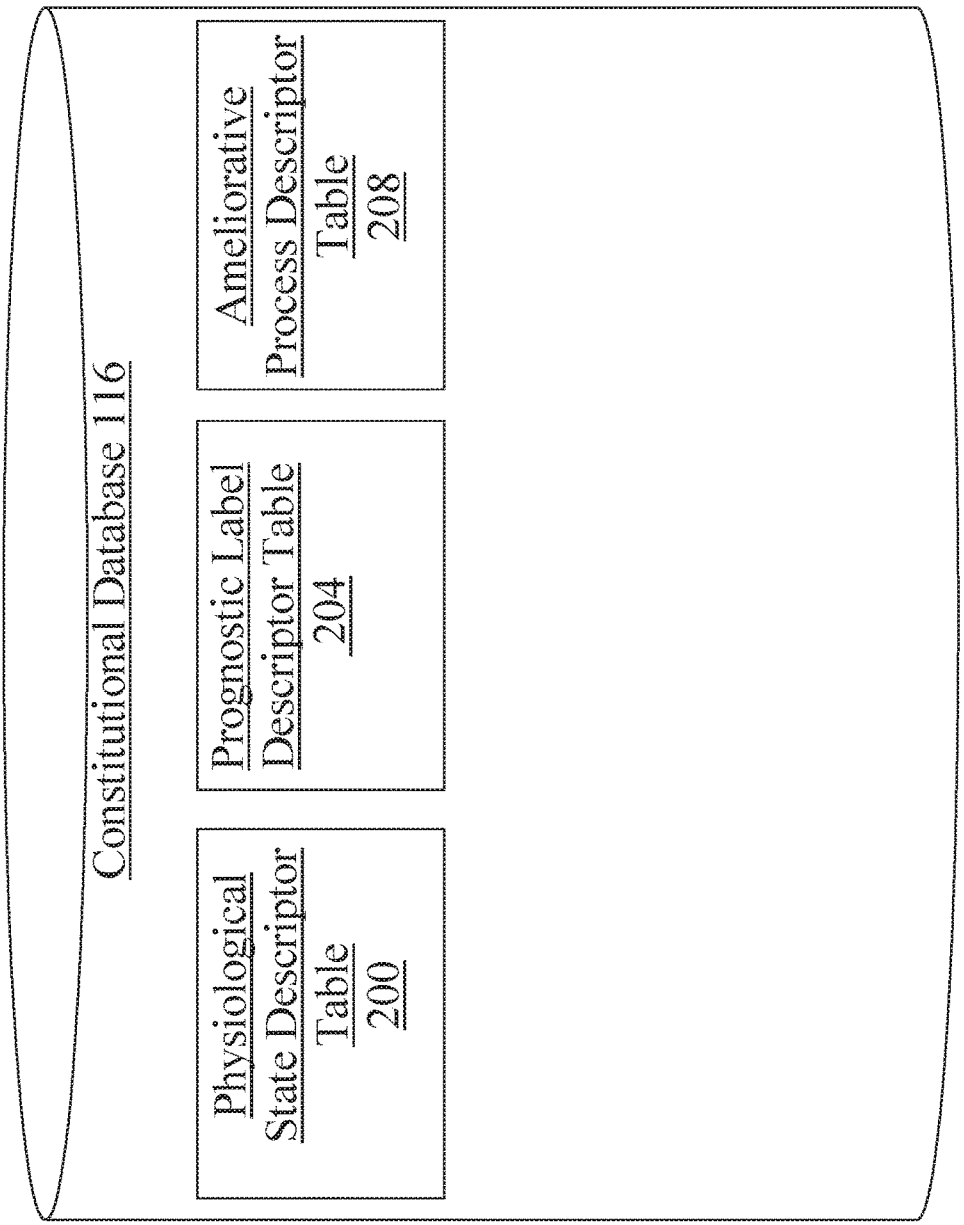
FIG. 2 is a block diagram illustrating an exemplary embodiment of a constitutional database.

Referring now to FIG. 2, data in constitutional database 116 may be stored in one or more tables. One or more tables of constitutional database 116 may include, without limitation, a physiological state descriptor table 200; physiological state descriptor table 200 may list textual descriptions corresponding to any kind of physiological state data, including one or more symptoms and/or clusters of symptoms, one or more biomarker values, or the like. Textual descriptions in physiological state descriptor table 200 may be used by expert submission processing module 108 to populate one or more prepopulated data entry fields as described above with textual descriptions of physiological state data; this may enable an expert to select standard-form data value for a datum of physiological state data, so that such selected values may be compared to constitutional inquiry values as described in further detail below. One or more tables of constitutional database 116 may include, without limitation, a prognostic label descriptor table 204; prognostic label descriptor table 204 may list textual descriptions corresponding to any kind of prognostic label data, including one or more diagnoses of current or potential future conditions, syndromes, or the like. Textual descriptions in prognostic label descriptor table 204 may be used by expert submission processing module 108 to populate one or more prepopulated data entry fields as described above with textual descriptions of prognostic label data; this may enable an expert to select standard-form data value for a datum of prognostic label data, so that such selected values may be compared to constitutional inquiry values as described in further detail below. One or more tables of constitutional database 116 may include, without limitation, an ameliorative process descriptor table 208; ameliorative process descriptor table 208 may list textual descriptions corresponding to any kind of ameliorative process data, including one or medical treatment processes, nutritional or exercise plans, or the like. Textual descriptions in ameliorative process descriptor table 208 may be used by expert submission processing module 108 to populate one or more prepopulated data entry fields as described above with textual descriptions of ameliorative process data; this may enable an expert to select standard-form data value for a datum of ameliorative process data, so that such selected values may be compared to constitutional inquiry values as described in further detail below. Persons skilled in the art, upon reviewing the entirety of this disclosure, will be aware of various alternative tables that may be used in constitutional database 116.

Referring again to FIG. 1, data used to auto-populate fields and/or to be matched to textual entries relating to one or more elements of ameliorative recommendation data may be stored in and/or retrieved from an ameliorative recommendation database 120, which may be implemented in any manner suitable for implementation of constitutional database 116.

Figure 3:
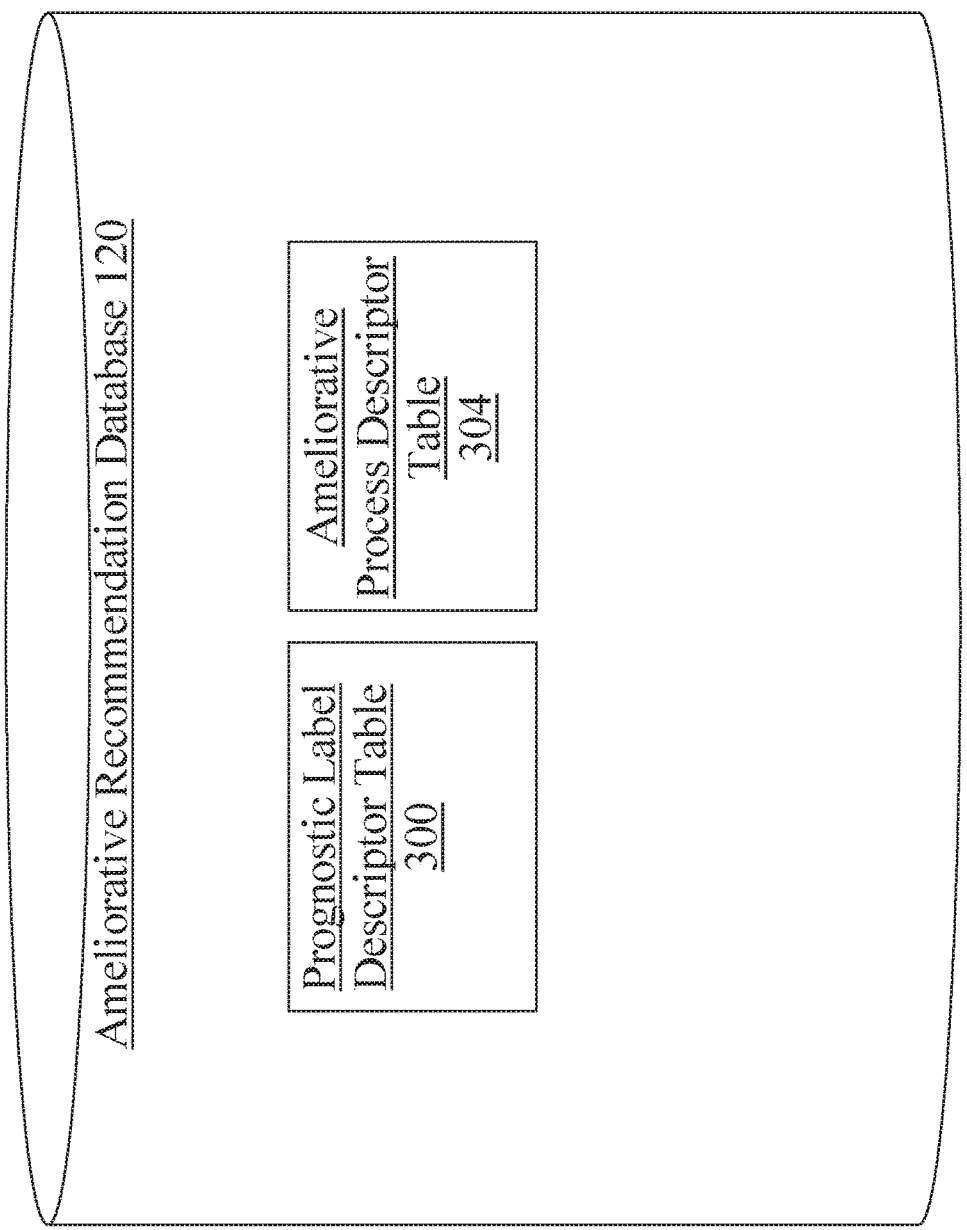
FIG. 3 is a block diagram illustrating an exemplary embodiment of an ameliorative recommendation database.

Referring now to FIG. 3, one or more tables of ameliorative recommendation database 120 may include, without limitation, a prognostic label descriptor table 300; prognostic label descriptor table 300 may list textual descriptions corresponding to any kind of prognostic label data, including one or more diagnoses of current or potential future conditions, syndromes, or the like. Textual descriptions in prognostic label descriptor table 300 may be used by expert submission processing module 108 to populate one or more prepopulated data entry fields as described above with textual descriptions of prognostic label data; this may enable an expert to select standard-form data value for a datum of prognostic label data, so that such selected values may be compared to ameliorative recommendation inquiry values as described in further detail below. One or more tables of ameliorative recommendation database 120 may include, without limitation, an ameliorative process descriptor table 304; ameliorative process descriptor table 304 may list textual descriptions corresponding to any kind of ameliorative process data, including one or medical treatment processes, nutritional or exercise plans, or the like. Textual descriptions in ameliorative process descriptor table 304 may be used by expert submission processing module 108 to populate one or more prepopulated data entry fields as described above with textual descriptions of ameliorative process data; this may enable an expert to select standard-form data value for a datum of ameliorative process data, so that such selected values may be compared to ameliorative recommendation inquiry values as described in further detail below. Persons skilled in the art, upon reviewing the entirety of this disclosure, will be aware of various alternative tables that may be used in ameliorative recommendation database 120.

Referring again to FIG. 1, expert submission processing module 108 may be configured to acquire an identity of the expert. Expert may, for instance, create a user account; expert may validate expert identity by any suitable means, including by providing identifying data such as biometric data, social security number, date of birth, one or more items of secret information such as answers to "security questions," or the like. Expert submission processing module 108 may be configured to query a listing of experts 124 using the identity. Listing of experts 124 may include any data structure suitable for listing and retrieval of data, including any database, datastore, hash table, linked list, or the like. Listing of experts 124 may be populated manually by an administrator of system 100 with some number of top-rated or most respected experts in a field. Listing of experts 124 may include tables describing specific areas of expertise corresponding to one or more experts; for instance, an expert may be listed on a table corresponding to functional medicine, but not on a table relating to ophthalmology, such that submissions from that expert may be eliminated where they relate to ophthalmological recommendations, but accepted related to recommendations pursuant to functional medicine. Expert submission processing module 108 may be configured to validate the expert based on a result of the query; in other words, where an expert is listed in the listing as corresponding to a field in which expert is posting an expert submission, the expert submission may be used for processes as described in further detail below, while if the submission pertains to a field in which expert is not listed, submission may be discarded. Fields may be identified by, for instance one or more tables and/or data structures linking particular prognostic labels and/or ameliorative processes to fields.

Continuing to refer to FIG. 1, in an embodiment, an expert submission may identify one or more additional experts to be "nominated" and/or otherwise proposed for listing on listing of experts 124 and/or listing on listing of experts 124 in connection with a given field. A drop-down list or similar prepopulated field may be used to list fields of expertise to be associated with a prospective expert. In an embodiment, where a threshold number, percentage, or other measurements of experts already in listing of experts 124 regarding the relevant field have entered a prospective expert, that expert may be added to the listing for that field. Persons skilled in the art, upon reviewing the entirety of this disclosure, will be aware of various alternative or additional ways in which listing of experts 124 may be populated, modified, and/or used consistently with this disclosure.

Still referring to FIG. 1, expert submission processing module 108 may be configured to receive the at least an expert submission by receiving at least a textual submission. At least a textual submission, as used in this disclosure, includes any document, including without limitation scientific journals, medical journals, articles, blog posts, books, and the like. At least a textual submission may be received using any form of electronic communication, including without limitation transfer of data over a network as described in this disclosure, reception from a memory storage device, manual entry by one or more users, scanning and/or optical character recognition, audio input with speech-to-text entry, or the like. In an embodiment, expert submission processing module 108 may be configured to receive the at least a textual submission by receiving the at least a textual submission from an expert client device. For instance, and without limitation, expert user interface 112 may provide an expert with a field in which to indicate a reference to a document describing constitutional data and/or ameliorative recommendation data as described in further detail below. Any data described above may alternatively or additionally be received from experts similarly organized in paper form, which may be captured and entered into data in a similar way, or in a textual form such as a portable document file (PDF) with examiner entries, or the like.

As a further non-limiting example, and still referring to FIG. 1, receiving the at least a textual submission may include acquiring an identity of at least an expert, identifying, in a document datastore 128, which may be a datastore of textual submissions 408, a textual submission authored by the at least an expert, using the identity of the at least an expert, and retrieving the textual submission from the document datastore 128. Document datastore 128 may be implemented in any manner suitable for implementation of constitutional database 116 as described above. Documents may be listed in document data store according to fields in which the documents are relevant and/or in which one or more authors of the documents are experts according to expert listing. Documents may be listed according to category of document; i.e., studies and/or journal articles may be differentiated from letters to the editor, popular science articles, or the like. Documents may be retrieved by citation, author name, field, or the like.

Referring again to FIG. 1, expert submission processing module 108 may be configured to extract at least an expert submission from the at least a textual submission. This may be performed in any suitable manner. For instance, and without limitation, expert submission processing module 108 further comprises a language processing module 132 designed and configured to convert the at least a textual submission into at least an expert submission. Language processing module 132 may include any hardware and/or software module. Language processing module 132 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 132 may compare extracted words to constitutional data and/or ameliorative recommendation data; such data for comparison may be entered on at least a server 104 as described above using expert data inputs or the like. In an embodiment, one or more elements of data may be enumerated, to find total count of mentions in such documents. Alternatively or additionally, language processing module 132 may operate to produce a language processing model. Language processing model may include a program automatically generated by at least a server 104 and/or language processing module 132 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words describing and/or including constitutional data and/or ameliorative recommendation data may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given element of constitutional data and/or ameliorative recommendation data; positive or negative indication may include an indication that a given document is or is not indicating an element of constitutional data and/or ameliorative recommendation data. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on at least a server 104, or the like.

Still referring to FIG. 1, language processing module 132 and/or at least a server 104 may generate a language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 132 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 132 may use a corpus of documents to generate associations between language elements in a language processing module 132, and at least a server 104 may then use such associations to analyze words extracted from one or more documents and determine that the one or more documents indicate significance of a category of physiological data, a given relationship of such categories to prognostic labels, and/or a given category of prognostic labels. In an embodiment, at least a server 104 may perform this analysis using a selected set of significant documents, such as documents identified by one or more experts as representing good science, good clinical analysis, or the like; experts may identify or enter such documents via expert user interface 112 as described above in reference to FIG. 1, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

With continued reference to FIG. 1, data received as part of at least an expert submission may be stored in an expert knowledge database 136. An expert knowledge database 136 may include any data structure and/or data store suitable for use as a constitutional database 116 as described above. Expert knowledge database 136 may include data entries reflecting one or more expert submissions of data such as may have been submitted according to any process described above in reference to FIG. 1, including without limitation by using first expert user interface 112. Expert knowledge database 136 may include one or more fields generated by language processing module 132, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 136 and linked to, entered in, or associated with entries in a physiological sample database. Documents may be stored and/or retrieved by at least a server 104 and/or language processing module 132 in and/or from a document database as described above; document database may include any data structure and/or data store suitable for use as physiological sample database as described above. Documents in document database may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
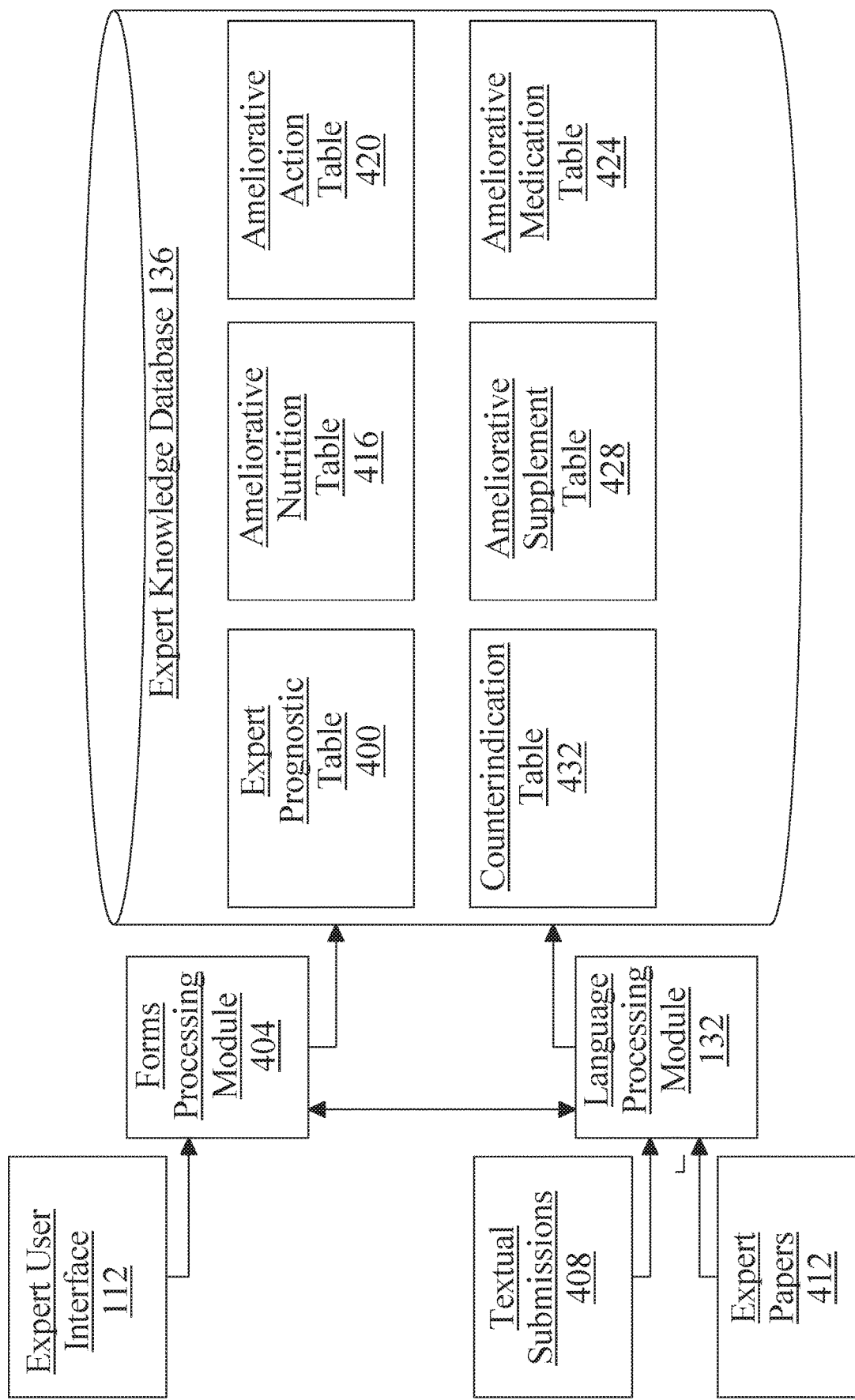
FIG. 4 is a block diagram illustrating an exemplary embodiment of an expert knowledge database.

Referring now to FIG. 4, an exemplary embodiment of an expert knowledge database 136 is illustrated. Expert knowledge database 136 may, as a non-limiting example, organize data stored in the expert knowledge database 136 according to one or more database tables. One or more database tables may be linked to one another by, for instance, common column values. For instance, a common column between two tables of expert knowledge database 136 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 136 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via expert user interface 112 as described above, one or more rows recording such an entry may be inserted in expert prognostic table 400. In an embodiment, a forms processing module 404 may sort data entered in a submission via expert user interface 112 by, for instance, sorting data from entries in the first expert user interface 112 to related categories of data; for instance, data entered in an entry relating in the first expert user interface 112 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 132 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 132 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 132. Data may be extracted from expert papers 412, which may include without limitation publications in medical and/or scientific journals, by language processing module 132 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 136 may include, as a further non-limiting example tables listing one or more ameliorative process labels; expert data populating such tables may be provided, without limitation, using any process described above, including entry of data from second expert user interface 112 via forms processing module 404 and/or language processing module 132, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 428 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 424 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 136 consistently with this disclosure.

In an embodiment, and still referring to FIG. 4, at least a server 104 may receive an update to one or more elements of data represented in expert submissions, expert knowledge database 136, or the like, and may perform one or more modifications to expert submissions, expert knowledge database 136, or other collections of data as described in this disclosure. For instance a physiological sample may turn out to have been erroneously recorded; at least a server 104 may remove it from data, as a result. As a further example, a medical and/or academic paper, or a study on which it was based, may be revoked; at least a server 104 may remove it from expert knowledge database 136, and/or document data store as a result. Information provided by an expert may likewise be removed if the expert loses credentials or is revealed to have acted fraudulently; expert may alternatively or additionally be removed from listing of experts 124 as related to one or more fields.

Continuing to refer to FIG. 4, elements of data of expert submissions and/or expert knowledge database 136 may have temporal attributes, such as timestamps; at least a server 104 may order such elements according to recency, select only elements more recently entered for training data and/or other processes as described below, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Continuing to refer to FIG. 1, system 100 includes a model generator 140 operating on the at least a server, the model generator 140 designed and configured to generate, using the at least an expert submission, and a constitutional inquiry, an ameliorative output. As used in this disclosure, a constitutional inquiry is an element of constitutional data as described above, and an ameliorative output is an element of ameliorative data related to the constitutional inquiry by at least an expert submission; in other words, ameliorative output may represent a "best practice" according to expert submission. For instance, and without limitation, where a constitutional inquiry includes a prognostic label corresponding to a particular condition, ameliorative output may represent one or more optimal treatment processes or protocols, as determined by expert opinions as reflected in at least an expert submission, for the condition and/or prospective condition represented by the prognostic label. As a further non-limiting example, where constitutional inquiry includes an element of physiological state data as described above, ameliorative output may include a prognostic label corresponding to a condition considered most likely, according to expert opinion, to be causing and/or related to the physiological state data, and/or ameliorative data representing an optimal treatment therefor.

Still referring to FIG. 1, system includes a client-interface module 144 operating on the at least a server 104; client-interface module 144 may include any suitable hardware and/or software module as described above. Client-interface module 144 is designed and configured to receive at least a constitutional inquiry from a user client device. Constitutional input may be received via a user entry in a user interface provided by client-interface device; user entry may be entered via a data entry field in a user-interface, such as a graphical user interface, provided by client-interface device, which may be performed as described above in relation to entry of at least an expert submission. For instance, a user may enter a constitutional inquiry describing a current or hypothetical condition, for instance with the aim of discovering one or more "best practice" treatment options for the condition. User providing entry may include a person who is inquiring about his or her own health, a medical professional trying to determine a best practice to use in treating a current, prospective, and/or hypothetical future patient, or the like.

Alternatively or additionally, and with continued reference to FIG. 1, constitutional inquiry may include at least a physiological test sample. At least a physiological test sample may include a physically extracted sample, which as used herein includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a physiological test sample may include at least a genetic sample. At least a genetic sample may include a complete genome of a person or any portion thereof. At least a genetic sample may include a DNA sample and/or an RNA sample. At least a physiological test sample may include an epigenetic sample, a proteomic sample, a tissue sample, a biopsy, and/or any other physically extracted sample. At least a physiological test sample may include an endocrinal sample. As a further non-limiting example, the at least a physiological test sample may include a signal from at least a sensor configured to detect physiological data of a user and recording the at least a physiological test sample as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of system 100 or may be a separate device in communication with system 100.

Still referring to FIG. 1, at least a physiological sample may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure In an embodiment, and still referring to FIG. 1, model generator 140 may be configured to generate ameliorative output by creating a query using the constitutional inquiry and querying expert knowledge database 136; model generator 140 may retrieve a result from expert knowledge database 136, and generate ameliorative output using the result. For instance, and without limitation, a user may enter constitutional inquiry using one or more pre-populated data entry forms such as drop-down lists or the like; the one or more pre-populated data entry forms may provide prepopulated entries corresponding to values stored in expert knowledge database 136, such that constitutional inquiry is automatically in the form of a query of expert knowledge database 136. In the above-described example, one or more records returned from expert knowledge database 136 may be presented by model generator 140 as ameliorative output. Constitutional inquiry entered in textual form may be matched to terms usable as a query of expert knowledge database 136 by language processing methods as described above, including without limitation vector similarity of constitutional inquiry textual data to canonical and/or database-linked data elements.

Alternatively or additionally, and continuing to refer to FIG. 1, model generator 140 may be configured to generate an ameliorative output by ranking a plurality of ameliorative outputs described in the ameliorative data and selecting the ameliorative output from the plurality of ameliorative outputs as a function of the ranking. For instance, one or more ameliorative outputs may be obtained from expert knowledge database 136 as described above, and/or otherwise obtained from at least an expert submission; ranking may be performed, for instance, by tallying expert submissions corresponding to each ameliorative output, such that ameliorative outputs having highest relative tallies, and/or tallies about a threshold amount, are selected as one or more ameliorative outputs to generate in response to constitutional inquiry.

Alternatively or additionally, and still referring to FIG. 1, model generator 140 may produce ameliorative output using machine learning. For instance, and without limitation, at least a server 104 and/or model generator may be designed and configured to convert at least an expert submission into training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Continuing to refer to FIG. 1, training data may alternatively or additionally include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, at least a server 104 may be configured to create training data including a plurality of data entries, each data entry of the at least an element of constitutional data and at least a correlated element of ameliorative data. In an embodiment, an element of constitutional data is correlated with an element of ameliorative data where the element of constitutional data is located in the same data element and/or portion of data element as the element of ameliorative data; for example, and without limitation, an element of constitutional data is correlated with a prognostic element where both element of constitutional data and prognostic element are contained within the same first data element of the training data. As a further example, an element of constitutional data is correlated with a prognostic element where both share a category label as described in further detail below, where each is within a certain distance of the other within an ordered collection of data in data element, or the like. Still further, an element of constitutional data may be correlated with an element of ameliorative data where the element of constitutional data and the element of ameliorative data share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between constitutional data and elements of ameliorative data that may exist in training data and/or first data element consistently with this disclosure. Correlation may be formed, without limitation, by an expert submission, which may link a given ameliorative datum to a given element of constitutional data as part of a recommendation by an expert, as described above.

In an embodiment, and still referring to FIG. 1, at least a server 104 may be designed and configured to associate at least an element of data in training set with at least a category from a list of significant categories of data. Significant categories of data may include labels and/or descriptors describing types of data that are identified as being of high relevance in identifying prognostic labels. As a non-limiting example, one or more categories may identify significant categories of based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert submission as described above.

Continuing to refer to FIG. 1, whether an entry indicating significance of a category of constitutional data, a given relationship of such categories to prognostic labels, and/or a given category of prognostic labels is entered via expert user interface 112, alternative submission means, and/or extracted from a document or body of documents as described above, an entry or entries may be aggregated to indicate an overall degree of significance. For instance, each category of constitutional data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of constitutional data, relationships of such categories to prognostic labels, and/or categories of prognostic labels may be ranked according significance scores, for instance by ranking categories of constitutional data, relationships of such categories to prognostic labels, and/or categories of prognostic labels higher according to higher significance scores and lower according to lower significance scores. Categories of constitutional data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of constitutional data, relationship of such category to prognostic labels, and/or category of prognostic labels is significant with regard to that test, while a second category of constitutional data, relationship of such category to prognostic labels, and/or category of prognostic labels is not significant; such indications may be used to perform a significance score for each category of constitutional data, relationship of such category to prognostic labels, and/or category of prognostic labels is or is not significant per type of physiological sample, which then may be subjected to ranking, comparison to thresholds and/or elimination as described above.

Still referring to FIG. 1, at least a server 104 may detect further significant categories of constitutional data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, training data may be populated by retrieval of one or more records from expert knowledge database 136; in an embodiment, entries retrieved from expert knowledge database 136 may be filtered and or select via query to match one or more additional elements of information as described above, so as to retrieve a training data including data belonging to a given cohort, demographic population, or other set, so as to generate outputs as described below that are tailored to a person or persons with regard to whom system 100 classifies constitutional data to ameliorative outputs as set forth in further detail below. Persons skilled in the art, upon reviewing the entirety of this disclosure, will be aware of various ways in which records may be retrieved from expert knowledge database 136 to generate training data to reflect individualized group data pertaining to a person of interest in operation of system and/or method, including without limitation a person with regard to whom at least a constitutional inquiry is being evaluated as described in further detail below. At least a server 104 may alternatively or additionally receive training data, for instance in the form of at least an expert submission, and store one or more entries in expert knowledge database 136 as extracted from elements of training data.

In an embodiment, and continuing to refer to FIG. 1, model generator 140 and/or at least a server 104 includes an expert learner 148, which may include any hardware or software module as described in this disclosure, configured to generate the ameliorative output using the at least an expert input and the at least a constitutional input using machine learning. Expert learner 148 may include any hardware and/or software module. Expert learner 148 may be designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Figure 5:
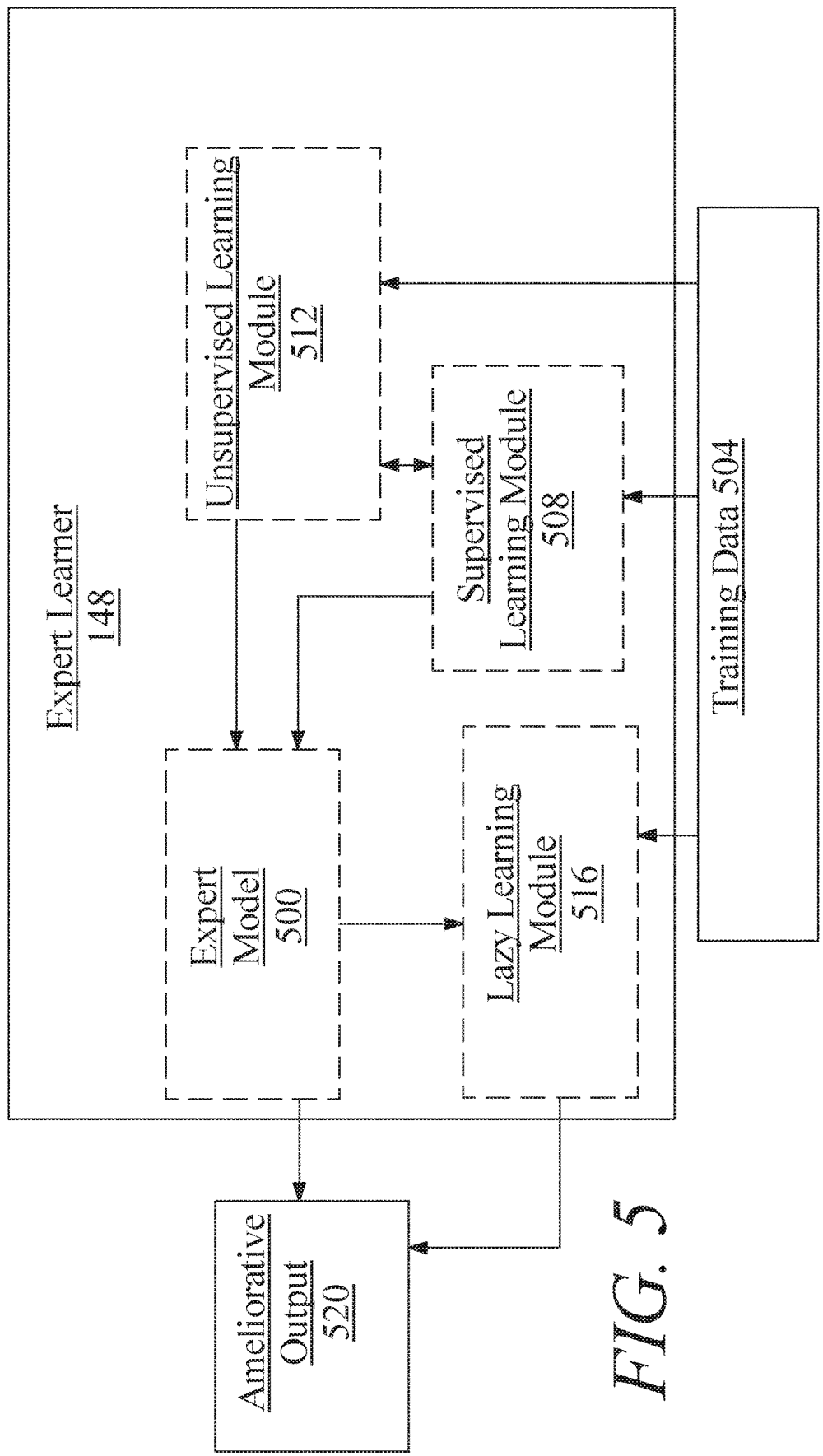
FIG. 5 is a block diagram illustrating an exemplary embodiment of an expert learner.

Referring now to FIG. 5, expert learner 148 may be designed and configured to generate at least an ameliorative output by creating expert learning model 500 relating constitutional data to elements of ameliorative data using training data and generating the at least a ameliorative output using the first machine-learning model; expert learning model 500 may include one or more models that determine a mathematical relationship between constitutional data and elements of ameliorative data. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 5, machine-learning algorithm used to generate first machine-learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 5, expert learner 148 may generate ameliorative output using artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data; the trained network may then be used to apply detected relationships between elements of constitutional data and elements of ameliorative data.

Referring now to FIG. 5, machine-learning algorithms used by expert learner 148 may include supervised machine-learning algorithms, which may, as a non-limiting example be executed using a supervised learning module 508 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, elements of ameliorative data as outputs, and a scoring function representing a desired form of relationship to be detected between elements of physiological data and elements of ameliorative data; scoring function may, for instance, seek to maximize the probability that a given element of constitutional data and/or combination of elements of physiological data is associated with a given element of ameliorative data and/or combination of elements of ameliorative data to minimize the probability that a given element of constitutional data and/or combination of elements of constitutional data is not associated with a given element of ameliorative data and/or combination of elements of ameliorative data. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of supervised machine learning algorithms that may be used to determine relation between elements of physiological data and elements of ameliorative data. In an embodiment, one or more supervised machine-learning algorithms may be restricted to a particular domain for instance, a supervised machine-learning process may be performed with respect to a given set of parameters and/or categories of parameters that have been suspected to be related to a given set of elements of ameliorative data, and/or are specified as linked to a medical specialty and/or field of medicine covering a particular set of elements of ameliorative data. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data 504. Domain restrictions may be suggested by experts and/or deduced from known purposes for particular evaluations and/or known tests used to evaluate elements of ameliorative data. Additional supervised learning processes may be performed without domain restrictions to detect, for instance, previously unknown and/or unsuspected relationships between physiological data and elements of ameliorative data.

Still referring to FIG. 5, machine-learning algorithms may include unsupervised processes; unsupervised processes may, as a non-limiting example, be executed by an unsupervised learning module 512 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, expert learner 148 and/or at least a server 104 may perform an unsupervised machine learning process on training data 504, which may cluster data of training data 504 according to detected relationships between elements of the training data 504, including without limitation correlations of elements of constitutional data to each other and correlations of elements of ameliorative data to each other; such relations may then be combined with supervised machine learning results to add new criteria for expert learner 148 to apply in relating constitutional data to elements of ameliorative data. As a non-limiting, illustrative example, an unsupervised process may determine that a first element of physiological data acquired in a blood test correlates closely with a second element of physiological data, where the first element has been linked via supervised learning processes to a given element of ameliorative data, but the second has not; for instance, the second element may not have been defined as an input for the supervised learning process, or may pertain to a domain outside of a domain limitation for the supervised learning process. Continuing the example a close correlation between first element of constitutional data and second element of constitutional data may indicate that the second element is also a good predictor for the element of ameliorative data; second element may be included in a new supervised process to derive a relationship or may be used as a synonym or proxy for the first physiological element by expert learner 148.

With continuing reference to FIG. 5, at least a server 104 and/or expert learner 148 may detect further significant categories of physiological data, relationships of such categories to elements of ameliorative data, and/or categories of elements of ameliorative data using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, expert learner 148 and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, elements of ameliorative data, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular elements of ameliorative data and/or suitable ameliorative labels. Use of unsupervised learning may greatly enhance the accuracy and detail with which system may detect elements of ameliorative data and/or ameliorative labels.

Still referring to FIG. 5, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of element of ameliorative data, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Continuing to refer to FIG. 5, expert learner 148 may alternatively or additionally be designed and configured to generate at least an ameliorative output by executing a lazy learning process as a function of the training data 504 and the at least a physiological test sample; lazy learning processes may be performed by a lazy learning module 516 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an element of ameliorative data associated with physiological test sample, using training data 504. As a non-limiting example, an initial heuristic may include a ranking of elements of ameliorative data according to relation to a test type of at least a physiological test sample, one or more categories of physiological data identified in test type of at least a physiological test sample, and/or one or more values detected in at least a physiological test sample; ranking may include, without limitation, ranking according to significance scores of associations between elements of physiological data and elements of ameliorative data, for instance as calculated as described above. Heuristic may include selecting some number of highest-ranking associations and/or elements of ameliorative data. Expert learner 148 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate ameliorative outputs as described in this disclosure, including without limitation lazy learning applications of machine-learning algorithms as described in further detail below.

In an embodiment, and still referring to FIG. 5, expert learner 148 may generate a plurality of elements of ameliorative data having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, expert learner 148 and/or at least a server 104 may perform additional processes to resolve ambiguity. Processes may include presenting multiple possible results to a medical practitioner, informing the medical practitioner that one or more follow-up tests and/or physiological samples are needed to further determine a more definite element of ameliorative data. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, expert learner 148 and/or at least a server 104 may operate a further algorithm to determine which of the multiple outputs is most likely to be correct; algorithm may include use of an additional supervised and/or unsupervised model. Alternatively or additionally, expert learner 148 may perform one or more lazy learning processes using a more comprehensive set of user data to identify a more probably correct result of the multiple results. Results may be presented and/or retained with rankings, for instance to advise a medical professional of the relative probabilities of various elements of ameliorative data being correct; alternatively or additionally, elements of ameliorative data associated with a probability of correctness below a given threshold and/or elements of ameliorative data contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of elements of ameliorative data associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of elements of ameliorative data on a list of multiple elements of ameliorative data, and/or to eliminate some labels from such a list. Ameliorative output 520 may be provided to user output device as described in further detail below.

Referring again to FIG. 1, client-interface module 144 may be designed and configured to transmit, to the user client device, the ameliorative output. Output may be displayed on a user client device using a user interface; user interface may display ameliorative output. Alternatively or additionally, ameliorative output may be translated into display data including without limitation textual descriptions corresponding to ameliorative output, one or more images associated with ameliorative output, and/or one or more video or audio files associated with ameliorative output; each of the above-described display data may be retrieved from a display data store, which may, for instance associate or link ameliorative output with one or more display data. Where output includes multiple ameliorative outputs, at least a server 104 may cause to a user output device to display the multiple labels and/or display data associated therewith; labels may be displayed according to rankings as described above, including without limitation rankings of ameliorative output as described above. Significance scores, as calculated above, may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated.

With continued reference to FIG. 1, at least a server 104 may be configured to display one or more follow-up suggestions at a user output device. One of more follow-up suggestions may include, without limitation, suggestions for acquisition of an additional physiological test sample; in an embodiment, additional physiological test sample may be provided to at least a server 104, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any physiological sample as described above.

With continued reference to FIG. 1, at least a server 104 may display one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with system 100. Contextual information may include one or more questions a patient wishes to have answered in a medical visit and/or session, and/or as a result of interaction with system 100. Contextual information may include one or more questions to ask a patient. Persons skilled in the art, upon reviewing the entirety of this disclosure, will be aware of various forms of contextual information that may be included, consistently with this disclosure. System 100 may record a conversation between a patient and a medical professional for later entry into medical records.

Embodiments of system 100 may furnish augmented intelligence systems that facilitate diagnostic, prognostic, curative, and/or therapeutic decisions by medical professionals such as doctors. Provision of expert system elements via expert inputs and document-driven language analysis may ensure that recommendations generated by system 100 are backed by the very best medical knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of medical visits; in embodiments, a comprehensive visit may be completed in as little as 10 minutes. Recommendations may further suggest follow up testing and/or therapy, ensuring an effective ongoing treatment and prognostic plan.

Figure 6:
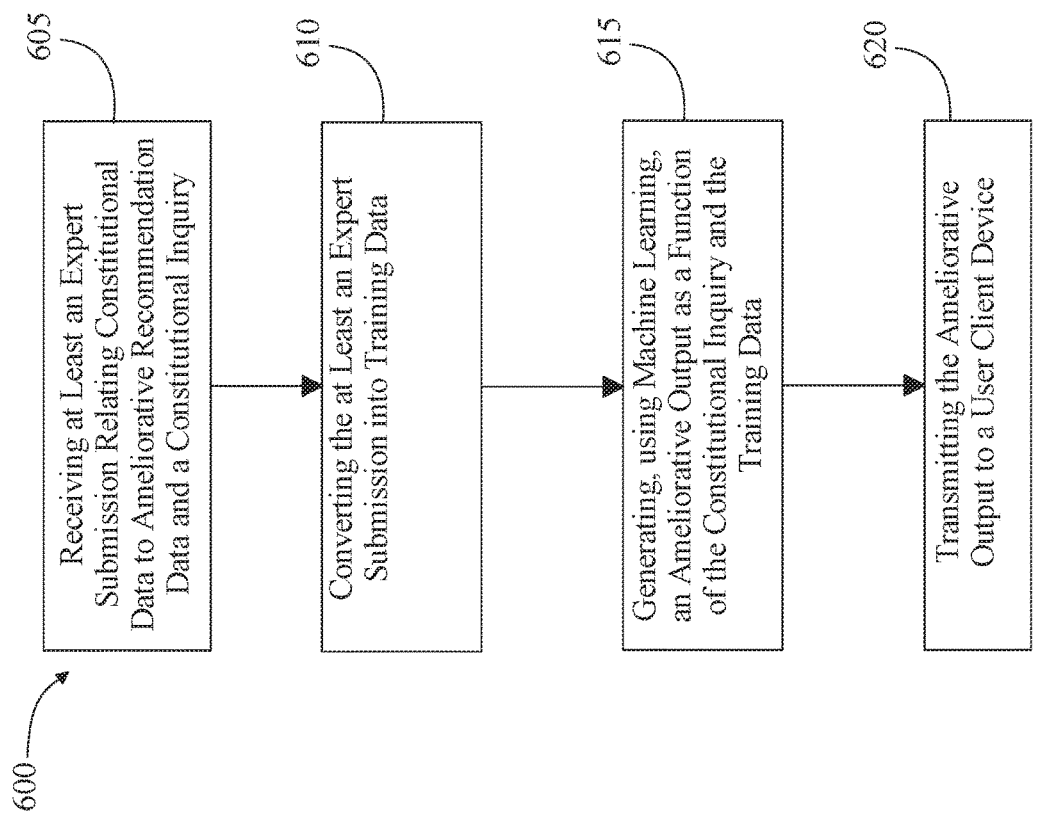
FIG. 6 illustrates flow diagram illustrating an exemplary embodiment of a method of classification using expert submissions.

Referring now to FIG. 6, an exemplary embodiment of a method 600 of classification using expert data is illustrated. At step 605, at least a server 104 receives at least an expert submission relating constitutional data to ameliorative recommendation data and a constitutional inquiry. In an embodiment, this may be performed as described above in reference to FIGS. 1-5. For example, and without limitation, receiving the at least an expert submission may include configuring an expert client device to display one or more data entry fields prompting an expert to input expert submission data and receiving, from the expert client device, at least a datum entered in the one or more data entry fields by the expert, for instance as described above in reference to FIGS. 1-5. Receiving the at least an expert submission may further include acquiring an identity of an expert querying a listing of experts 124 using the identity, and validating the expert based on a result of the query, for instance as described above in reference to FIGS. 1-5.

As a further non-limiting example, and still referring to FIG. 6, receiving at least an expert submission may include receiving at least a textual submission and extracting the at least an expert submission from the at least a textual submission; this may be implemented as described above in reference to FIGS. 1-5. Receiving at least a textual submission may include receiving the at least a textual submission from an expert client device, for instance as described above in reference to FIGS. 1-5. Receiving at least a textual submission may include, as a further non-limiting example, acquiring an identity of at least an expert, identifying, in a document datastore 128, a textual submission authored by the at least an expert, using the identity of the at least an expert, and retrieving the textual submission from the document datastore 128, for instance as described above in reference to FIGS. 1-5. Method 600 may further include converting, using a language processing module 132, the at least a textual submission into at least an expert submission; this may be implemented as described above in reference to FIGS. 1-5.

At step 610, and still referring to FIG. 6, at least a server 104 converts the at least an expert submission into training data. This may be performed, without limitation, as described above in reference to FIGS. 1-5.

At step 615, and with continued reference to FIG. 6, at least a server 104 generates an ameliorative output as a function of the constitutional inquiry and the training data using machine learning. This may be implemented, without limitation, as described above in reference to FIGS. 1-5. As a non-limiting example, generating the ameliorative output may include ranking a plurality of ameliorative outputs described in the ameliorative data and selecting the ameliorative output from the plurality of ameliorative outputs as a function of the ranking, for instance as described above in reference to FIGS. 1-5. As a further non-limiting example, generating the ameliorative output may include generating the ameliorative output via a machine-learning process using the at least an expert input and the at least a constitutional input, for instance as described above in reference to FIGS. 1-5. As an additional example, and without limitation, generating the ameliorative output may include generating at least an expert model as a function of the at least an expert input, for instance as described above in reference to FIGS. 1-5.

At step 620, and still referring to FIG. 6, at least a server 104 transmits the ameliorative output to a user client device; this may be implemented as described above in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
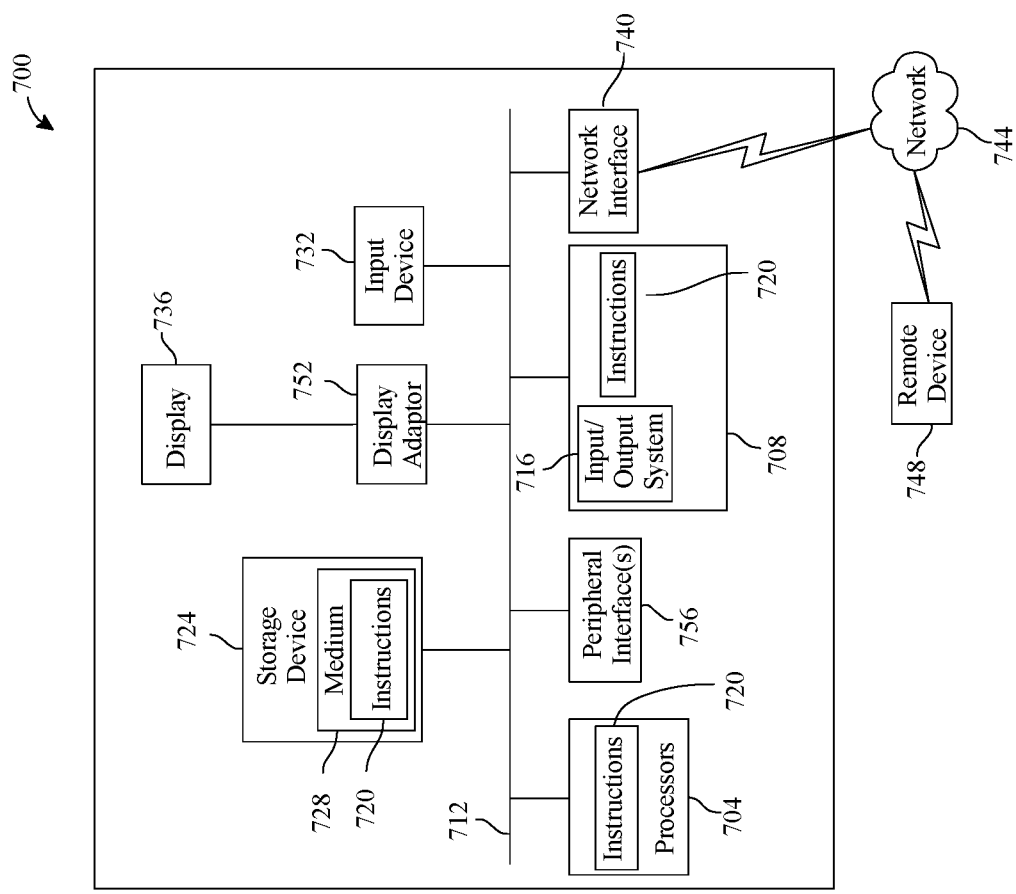
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for classification using expert data, the system comprising:
    a processor;
    an expert submission processing module operating on the processor, the expert submission processing module designed and configured to:
        receive an expert submission relating constitutional data to ameliorative recommendation data, wherein said expert submission is associated with an expert; and
        determine whether to associate the expert with a field of expertise, wherein said determination is derived from a listing of experts identifying a plurality of experts associated with the field of expertise;
    a model generator operating on the processor, the model generator designed and configured to convert the expert submission into training data;
    an expert learner operating on the processor, wherein the expert learner is configured to:
        determine a category of physiological data from the expert submission;
        generate, using a machine learning process, an ameliorative output as a function of the training data and a constitutional inquiry, wherein the ameliorative output comprises a therapy; and
        generate a significance score related to the ameliorative output based on the determined category of physiological data, wherein the significance score represents an association between the therapy and the category of physiological data from the expert submission;
    a client-interface module operating on the processor, the client-interface module designed and configured to:
        receive, from a user client device associated with the user, the constitutional inquiry; and
        transmit, to the user client device associated with the user, the ameliorative output.

2. The system of claim 1, wherein the expert submission processing module further comprises an expert user interface designed and configured to:
    configure an expert client device to display one or more data entry fields, wherein said one or more data entry fields comprise a prompt for expert submission data; and
    receive, from the expert client device, at least a datum, wherein the at least a datum is received as an interaction with the one or more data entry fields.

3. The system of claim 2, wherein the expert submission processing module is further configured to:
    acquire an identity of the expert;
    query a listing of experts using the identity; and
    validate the expert based on a result of the query.

4. The system of claim 1, wherein the expert submission processing module is further configured to:
    receive at least a textual submission; and
    extract the expert submission from the at least a textual submission.

5. The system of claim 4, wherein receiving the at least a textual submission further comprises receiving the at least a textual submission from an expert client device.

6. The system of claim 4, wherein receiving the at least a textual submission further comprises:
    acquiring an identity of at least an expert;

identifying, in a document datastore, a textual submission authored by the at least an expert, using the identity of the at least an expert; and retrieving the textual submission from the document datastore.

7. The system of claim 4, wherein the expert submission processing module further comprises a language processing module designed and configured to convert the at least a textual submission into the expert submission.

8. The system of claim 1, wherein the model generator is configured to generate the ameliorative output by:

ranking a plurality of ameliorative outputs described in the ameliorative data; and selecting the ameliorative output from the plurality of ameliorative outputs as a function of the ranking.

9. The system of claim 1, wherein the expert learner is configured to generate at least an expert model as a function of the training data.

10. The system of claim 1, wherein the expert learner is configured to generate the at least an ameliorative output using a lazy learning protocol as a function of the training data and the constitutional inquiry.

11. A method of classification using expert data, the method comprising:

receiving, by a processor, an expert submission relating constitutional data to ameliorative recommendation data and a constitutional inquiry, wherein said expert submission is associated with an expert;

determining, by the processor, whether to associate the expert with a field of expertise, wherein said determination is derived from a listing of experts identifying a plurality of experts associated with the field of expertise;

converting, by the processor, the expert submission into training data;

determining a category of physiological data from the expert submission;

generating, by the processor, using machine learning, an ameliorative output as a function of the constitutional inquiry and the training data wherein the ameliorative output comprises a therapy;

generating a significance score related to the ameliorative output based on the determined category of physiological data, wherein the significance score represents an association between the therapy and the category of physiological data from the expert submission; and transmitting, by the processor and to the user client device associated with the user, the ameliorative output, wherein the ameliorative output in configured to display the condition of the user and the treatment associated with the condition on the user client device.

12. The method of claim 11, wherein receiving the expert submission further comprises:

configuring an expert client device to display one or more data entry fields, where said one or more data entry fields comprise a prompt for expert submission data; and receiving, from the expert client device, at least a datum, wherein the at least a datum is received as an interaction with the one or more data entry fields.

13. The system of claim 12 further comprising:

acquiring an identity of the expert;

querying a listing of experts using the identity; and validating the expert based on a result of the query.

14. The method of claim 11, wherein receiving the expert submission further comprises:

receiving at least a textual submission; and extracting the expert submission from the at least a textual submission.

15. The method of claim 14, wherein receiving the at least a textual submission further comprises receiving the at least a textual submission from an expert client device.

16. The method of claim 14, wherein receiving the at least a textual submission further comprises:

acquiring an identity of at least an expert;

identifying, in a document datastore, a textual submission authored by the expert, using according to the identity of the at least an expert; and retrieving the textual submission from the document datastore.

17. The method of claim 14, further comprising converting, using a language processing module, the at least a textual submission into the expert submission.

18. The method of claim 11, wherein generating the ameliorative output further comprises:

ranking a plurality of ameliorative outputs described in the ameliorative data; and selecting the ameliorative output from the plurality of ameliorative outputs as a function of the ranking.

19. The method of claim 11, wherein generating the at least an ameliorative output further comprises generating at least an expert model as a function of the training data.

20. The method of claim 11 wherein generating the at least an ameliorative output further comprises generating the at least an ameliorative output using a lazy learning protocol as a function of the training data and the constitutional inquiry.

* * * * *